(12) United States Patent  
Drennan

(10) Patent No.: US 8,444,584 B2
(45) Date of Patent: May 21, 2013

(54) METHOD AND COMPRESSION HOSE FOR RELIEVING HEEL PRESSURE

(75) Inventor: Denis Burke Drennan, Evanston, IL (US)

(73) Assignee: DM Systems Inc., Evanston, IL (US)

( * ) Notice: Subject to any disclaimer, the term of this patent is extended or adjusted under 35 U.S.C. 154(b) by 197 days.

(21) Appl. No.: 12/873,746

(22) Filed: Sep. 1, 2010

(65) Prior Publication Data

US 2011/0054376 A1    Mar. 3, 2011

Related U.S. Application Data

(60) Provisional application No. 61/238,817, filed on Sep. 1, 2009, provisional application No. 61/024,692, filed on Jan. 30, 2008.

(51) Int. Cl.
*A61F 13/00* (2006.01)
*A41B 11/00* (2006.01)

(52) U.S. Cl.
USPC .................. 602/63; 602/60; 602/61; 602/62; 2/239

(58) Field of Classification Search
USPC .................. 602/60–64; 66/17, 18; 2/239
See application file for complete search history.

(56) References Cited

U.S. PATENT DOCUMENTS

| 1,659,934 | A | * | 2/1928 | Willmott | 66/178 R |
|---|---|---|---|---|---|
| 1,786,862 | A | * | 12/1930 | Mouthe | 66/178 R |
| 1,815,667 | A | * | 7/1931 | Damon | 66/178 R |
| 1,836,679 | A | * | 12/1931 | Mouthe | 66/187 |
| 1,887,927 | A | * | 11/1932 | Fox | 66/189 |
| 1,968,832 | A | * | 8/1934 | Hinchliff | 2/239 |
| 2,109,134 | A | * | 2/1938 | Kendrick | 2/239 |
| 2,334,206 | A | * | 11/1943 | Knohl | 66/187 |
| 3,856,008 | A |  | 12/1974 | Fowler et al. |  |
| 4,027,667 | A |  | 6/1977 | Swallow et al. |  |
| 4,172,456 | A |  | 10/1979 | Zens |  |
| 4,502,301 | A | * | 3/1985 | Swallow et al. | 66/178 A |
| 5,005,567 | A |  | 4/1991 | Gilman et al. |  |
| 5,139,475 | A |  | 8/1992 | Robicsek |  |
| 6,123,681 | A |  | 9/2000 | Brown, III |  |
| 6,135,974 | A | * | 10/2000 | Matz | 602/62 |
| 6,311,334 | B1 |  | 11/2001 | Reinhardt et al. |  |
| 6,684,412 | B2 |  | 2/2004 | Ricci et al. |  |
| 6,725,691 | B2 |  | 4/2004 | Yakopson |  |

* cited by examiner

*Primary Examiner* — Kim M Lewis

(74) *Attorney, Agent, or Firm* — Hartman Global IP Law; Gary M. Hartman; Domenica N. S. Hartman

(57) ABSTRACT

A compression hose adapted to be worn to cover at least the calf and foot of a leg of an individual, and a method for medically treating the individual with the compression hose. The compression hose includes connected leg and foot portions formed of an elastic fabric material and adapted to cover, respectively, the calf and foot of the individual. A heel opening is located between the leg and foot portions so as to be located in the compression hose to coincide with the heel of the leg of the individual. The heel opening has a perimeter defined by a stitch that limits stretching and expansion of the heel opening relative to stretching and expansion of the leg and foot portions of the compression hose.

18 Claims, 1 Drawing Sheet

METHOD AND COMPRESSION HOSE FOR RELIEVING HEEL PRESSURE

CROSS REFERENCE TO RELATED APPLICATIONS

This application claims the benefit of U.S. Provisional Application No. 61/238,817, filed Sep. 1, 2009, the contents of which are incorporated herein by reference. In addition, this application is related to U.S. Provisional Application No. 61/024,692, filed Jan. 30, 2008, the contents of which are incorporated herein by reference.

BACKGROUND OF THE INVENTION

The present invention generally relates to compression hoses (stockings), and more particularly to anti-embolism compression stockings, commonly referred to as TED (thrombo-embolic deterrent) hoses.

Compression hoses have been developed that are intended to be worn by ambulatory and nonambulatory patients. The constructions of compression hoses differ on the basis of their different intended functions and uses. For example, TED hoses are typically designed to be worn by recumbent and bedridden individuals, for example, post-surgical patients, to provide substantially uniform compression levels around the ankle and on the calf above the ankle for the purpose of supporting the venous system within the leg.

FIG. 1 depicts an example of a TED hose used by hospitals to aid in the prevention of deep vein thrombosis (DVT). The type of TED hose illustrated in FIG. 1 is typically designed to apply a compression level of about 10 to 20 mm Hg pressure to the calf and across the ankle, compared to typical compression levels of about 20 to 30 mm Hg applied by compression hoses intended to treat severe venous diseases. As can be appreciated from FIG. 1, the TED hose applies compression over the entire heel, including the back of the heel and surrounding tissues.

BRIEF DESCRIPTION OF THE INVENTION

The present invention provides a compression hose adapted to be worn to cover at least the calf and foot of a leg of an individual, and a method for medically treating the individual with the hose.

According to a first aspect of the invention, the hose includes connected leg and foot portions formed of an elastic fabric material and adapted to cover, respectively, the calf and foot of the individual, and a heel opening located between the leg and foot portions so as to be located in the hose to coincide with the heel of the leg of the individual. The heel opening has a perimeter defined by a stitch that limits stretching and expansion of the heel opening relative to stretching and expansion of the leg and foot portions of the hose.

Another aspect of the invention is a method of treating the individual with the hose described above. In particular, the hose is positioned on a leg of the individual so that the leg and foot portions cover, respectively, the calf and foot of the individual and the heel opening coincides with the heel of the leg. As a result of the hose being positioned on the leg, the heel opening expands and the heel protrudes through the expanded heel opening.

In view of the above, it can be seen that the heel opening prevents the hose from applying any pressure to the heel. In this manner, the risk of damage to the posterior heel tissues is reduced and heel pressure ulcers can be avoided in nonambulatory and particularly bedridden patients.

Other aspects and advantages of this invention will be better appreciated from the following detailed description.

DETAILED DESCRIPTION OF THE INVENTION

Figure 1:
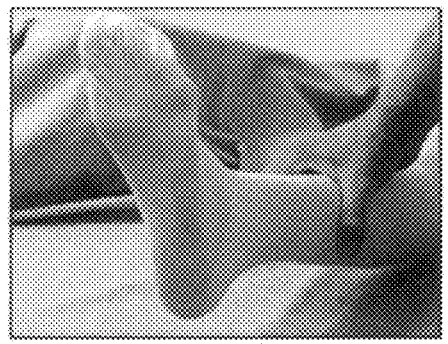
FIG. 1 depicts a TED hose of a type known in the prior art.

Investigations leading up to the present invention showed that a TED hose of the type shown in FIG. 1 is likely to apply compression to the heel of an individual at levels significantly higher than the compression level applied by the hose to the individual's calf. For example, a TED hose that applies a typical compression level of about 13 mm Hg pressure to the calf is likely to apply compression of about 18 mm Hg pressure over the heel.

The capillary circulation and $pcO_2$ (partial pressure of oxygen) in the posterior heel tissues become compromised if subjected to pressures above about 32 mm Hg for prolonged periods of time. Therefore, a prior art TED hose of the type represented in FIG. 1 that applies compression of about 18 mm Hg pressure over the heel may endanger the posterior heel tissues if the heel is allowed to rest on a support surface, such as a bed. This situation may be an element in the high incidence of heel pressure ulcers in elderly bedridden patients, as well as postoperative and post trauma patients. Though the foot can be raised to relieve the heel pressure applied by a bed, compliance is often difficult.

Figure 2:
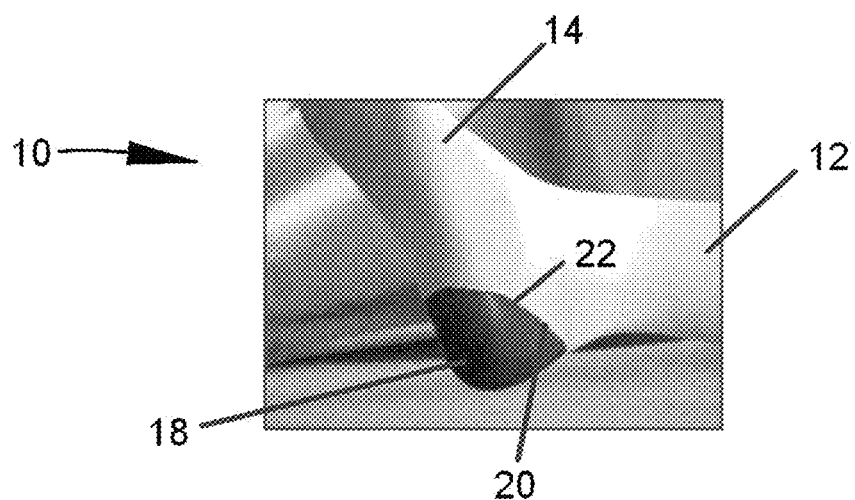
FIG. 2 represents a TED hose in accordance with an embodiment of this invention.

FIG. 2 represents a TED hose 10 according to an embodiment of the invention. As with prior art TED hoses of the type shown in FIG. 1, the TED hose 10 comprises a leg portion 12 sized to cover at least the calf of an individual, and a foot portion 14 that is connected to the leg portion 12 and intended to cover the foot and ankle of an individual. As is also conventional, the leg portion 12 defines an opening (not shown) through which an individual's foot passes as the hose 10 is donned. The foot portion 14 may also have an opening in the toe region through which the individual's toes are exposed. However, in contrast to conventional TED hoses of the type shown in FIG. 1, the TED hose 10 lacks a heel portion that would cover the heel 18 of a patient. Instead, the hose 10 has a round opening 20 that, when the hose 10 is worn, is aligned with the individual's heel 18 so that the entire heel 18, including the back of the heel 18 and surrounding regions, protrudes through the opening 20. As such, the heel opening 20 eliminates all pressure that would be otherwise applied by the hose 10 at the patient's heel 12. As such, the TED hose 10 is configured as an anti-embolism product that relieves the added heel pressure applied by conventional TED hoses, for example, of the type shown in FIG. 1. The TED hose 10 of FIG. 2 is an alternative to making a cut of poorly-controlled size in the heel portion of an otherwise conventional TED hose, and in particular provides the capability of the opening 20 being appropriately sized and shaped to ensure that pressure is not applied at the patient's heel 18 without compromising the application of pressure at therapeutic levels (for example, up to about 20 mm Hg, preferably about 10 to 20 mm Hg) to the ankle and calf.

The TED hose 10 can be fabricated from a variety of elastic fabric materials, including the same materials used in conventional compression stockings, including conventional TED hoses. Also consistent with conventional compression stockings, the leg and foot portions 12 and 14 of the hose 10 can be formed as a unitary piece of the same elastic fabric material. In preferred embodiments the perimeter of the opening 20 is defined by a stitch 22 formed of an elastic or inelastic yarn material that limits the stretching and expansion of the opening 20 relative to something less than the stretching and expansion that can be achieved in the remainder of the hose 10, such that the size and shape of the opening 20 can be more controllably defined to accommodate a limited range of foot sizes. In this manner, the TED hose 10 can be manufactured in a range of small, medium and large sizes, and the opening 20 appropriately sized to ensure that the entire heel of the wearer will be exposed. A nonlimiting example of an effective size for the opening 20 is a relaxed diameter of about five centimeters. Sizes in a range of, for example, ±50% of five centimeters, would presumably accommodate the heels of a wide range of potential wearers.

Elastic fiber materials similar to or the same as the elastic fabric material of the hose 10 are believed to be preferred for the stitch material to enable the opening 20 to more readily accommodate variable patients. For example, the stitch 22 may allow the opening 20 to expand to about 200% of its relaxed size. As a nonlimiting example, an opening 20 having a relaxed diameter of about five centimeters would be capable of being stretched and expanded to a diameter of about ten centimeters. The stitch material is preferably sewn flat without a high raised edge so that the stitch 22 does not create a pressure point on the heel 18.

As noted above, the opening 20 of the TED hose 10 preferably has a round shape, including circular and oval shapes, generally defined by a cutout of the elastic material of the hose 10 and generally corresponding to the shape of the heel 18. Alternatively, the TED hose 10 can be manufactured so that the opening 20 is in the form of a vertical slit in the elastic material of the hose 10, in other words, in the direction from the back of the heel 18, over the heel 18 and toward the toe. The opening 20 could also be manufactured as a horizontal slit in the elastic material of the hose 10, in other words, across the heel 18 from side to side (transverse). A combination of vertical and horizontal slits could also be used to define the opening 20, resulting in the opening 20 having a stellate shape. Yet another option is for the opening 20 to be loosely covered by a saccular outpouching of the elastic material of the hose 10 such that the material forming the outpouching does not apply pressure to the heel 18.

The opening 20 can also provide additional benefits, including easier and continuous visualization of the heel 18, which allows the heel to be visualized for signs of pressure injury. The opening 20 also allows for palpation of the heel 18 and the application of skin moisturizers and other protective lotions.

While the invention has been described in terms of particular embodiments, it is apparent that other forms could be adopted by one skilled in the art. For example, the hose could differ in appearance and construction from the embodiment shown in FIG. 2, and various appropriate materials could be used to form the hose 10. Therefore, the scope of the invention is to be limited only by the following claims.

The invention claimed is:

1. A compression hose adapted to be worn to cover at least the calf and foot of a leg of an individual, the compression hose comprising:
   leg and foot portions formed by a unitary piece of an elastic fabric material and adapted to cover, respectively, the calf and foot of the individual; and
   an opening located in the unitary piece between the leg and foot portions so as to be located at a heel of the leg of the individual, the opening having a perimeter defined by a stitch sewn in the unitary piece by an elastic fiber material, the stitch being sewn flat so that the stitch does not create a pressure point when the compression hose is worn on the leg of the individual, the opening having an oval shape so as to have a side-to-side orientation relative to the heel when the compression hose is worn on the leg of the individual.

2. The compression hose according to claim 1, wherein the heel opening has a relaxed diameter of about five centimeters ±50%.

3. The compression hose according to claim 1, wherein the stitch allows stretching and expansion of the opening to about 200% of its relaxed dimension.

4. The compression hose according to claim 1, wherein the opening has an expanded dimension of about ten centimeters.

5. The compression hose according to claim 1, wherein the stitch is formed of an elastic yarn material.

6. The compression hose according to claim 1, wherein the leg and foot portions of the compression hose apply up to about 20 mm Hg pressure to the calf and foot of the individual and the compression hose does not apply any pressure to the heel as a result of the opening.

7. The compression hose according to claim 1, wherein the leg and foot portions of the compression hose apply about 10 to 20 mm Hg pressure to the calf and foot of the individual and the compression hose does not apply any pressure to the heel as a result of the opening.

8. A method of medically treating an individual using the compression hose adapted to be worn to cover at least a calf and foot of a leg of the individual, the compression hose comprising leg and foot portions formed by a unitary piece of an elastic fabric material and adapted to cover, respectively, the calf and foot of the individual, the compression hose further comprising an opening located in the unitary piece between the leg and foot portions so as to be located at a heel of the leg of the individual, the opening having a perimeter defined by a stitch sewn in the unitary piece by an elastic fiber material, the stitch being sewn flat so that the stitch does not create a pressure point when the compression hose is worn on the leg of the individual, the opening having an oval shape so as to have a side-to-side orientation relative to the heel when the compression hose is worn on the leg of the individual, the method comprising positioning the compression hose on the leg of the individual so that the leg and foot portions cover, respectively, the calf and the foot of the individual, the opening coincides with the heel of the leg of the individual, and the opening stretches and expands less than stretching and expansion that occurs in the leg and foot portions of the compression hose.

9. The method according to claim 8, wherein the opening has a relaxed diameter of about five centimeters±50% prior to the compression hose being positioned on the leg of the individual.

10. The method according to claim 8, wherein the stitch allows stretching and expansion of the opening to about 200% of its relaxed diameter.

11. The method according to claim 8, wherein the opening has an expanded dimension of about ten centimeters after the compression hose is positioned on the leg of the individual.

12. The method according to claim 8, wherein the leg and foot portions of the compression hose apply up to about 20 mm Hg pressure to the calf and foot of the individual and the compression hose does not apply any pressure to the heel as a result of the opening.

13. The method according to claim 8, wherein the leg and foot portions of the compression hose apply about 10 to 20 mm Hg pressure to the calf and foot of the individual and the compression hose does not apply any pressure to the heel as a result of the opening.

14. The method according to claim 8, wherein the medical treatment is performed to prevent deep vein thrombosis.

15. The method according to claim 8, wherein the medical treatment is performed while the individual is nonambulatory.

16. The method according to claim 15, wherein the medical treatment is performed while the individual is recumbent.

17. The method according to claim 16, wherein the medical treatment is performed while the individual is bedridden.

18. The method according to claim 17, wherein the individual is a post-surgical patient.

* * * * *